United States Patent [19]

Soudant

[11] Patent Number: 5,658,576
[45] Date of Patent: Aug. 19, 1997

[54] METHOD FOR COMBATTING CELLULITIS OR REDUCING LOCALIZED FATTY EXCESSES

[75] Inventor: Etienne Soudant, Fresnes, France

[73] Assignee: L'Oreal, Paris, France

[21] Appl. No.: 307,071

[22] Filed: Sep. 16, 1994

Related U.S. Application Data

[63] Continuation of Ser. No. 80,847, Jun. 24, 1993, abandoned, which is a continuation-in-part of Ser. No. 436,889, Nov. 15, 1989, abandoned.

[51] Int. Cl.⁶ .............................. A61K 7/00; A61K 9/00
[52] U.S. Cl. .................... 424/401; 424/436; 424/456; 424/464; 424/489; 514/356; 514/510; 514/937; 514/962; 514/966
[58] Field of Search .................... 424/401, 464, 424/456, 489, 436; 514/937, 962, 966, 356, 510

[56] References Cited

U.S. PATENT DOCUMENTS

| | | | |
|---|---|---|---|
| 4,795,638 | 1/1989 | Ayache et al. | 424/195.1 |
| 4,837,214 | 6/1989 | Tanaka | 424/401 |
| 4,938,960 | 7/1990 | Ismail | 424/195.1 |
| 5,030,451 | 7/1991 | Trebosc et al. | 424/401 |
| 5,165,935 | 11/1992 | Andre et al. | 414/401 |
| 5,194,259 | 3/1993 | Soudant et al. | 424/401 |
| 5,215,759 | 6/1993 | Mausner | 424/489 |
| 5,340,579 | 8/1994 | Casero | 514/2 |
| 5,362,494 | 11/1994 | Zysman et al. | 424/401 |
| 5,523,090 | 6/1996 | Znaiden et al. | 424/401 |
| 5,536,499 | 7/1996 | Znaiden et al. | 424/401 |

FOREIGN PATENT DOCUMENTS

| | | |
|---|---|---|
| 0220825 | 9/1989 | European Pat. Off. . |
| 2105254 | 3/1974 | France . |
| 195316 | 8/1987 | Japan . |
| 2002232 | 2/1979 | United Kingdom . |
| 2002233 | 2/1979 | United Kingdom . |

OTHER PUBLICATIONS

Patent Abstract of Japan, vol. 10, No. 339 (C–385) (2395), Nov. 15, 1986 & JA-A- 62 143 311.
Patent Abstract of Japan, vol. 12, No. 47 (C–475) Feb. 12, 1988 & JA-A-62 195 316.
Parfumerie Und Kosmetik, vol. 68 No. 9, 1987, pp. 540, 543–544, Vogel, et al "Vitamin–E–Nikotinat – Ein Neuer Wirkstoff Fur Die Kosmetik".

*Primary Examiner*—Amy Hulina
*Attorney, Agent, or Firm*—Cushman Darby & Cushman IP Group of Pillsbury, Madison & Sutro, LLP

[57] ABSTRACT

A method for combatting cellulitis or reducing localized fatty excesses involves administering a body slimming amount of a composition which contains, as the sole slimming agent, an α-tocopherol, benzyl, xanthinol or hexyl nicotinate, or α-tocopherol acetate.

8 Claims, No Drawings

METHOD FOR COMBATTING CELLULITIS OR REDUCING LOCALIZED FATTY EXCESSES

This is a continuation of application Ser. No. 08/080,847, filed Jun. 24, 1993, now abandoned is a continuation-in-part of application Ser. No. 07/436,889 filed Nov. 15, 1989, now abandoned.

The present invention relates to a method for combatting cellulitis or reducing localized fatty excesses which comprises administering to a person having cellulitis or localized fatty excesses a body slimming amount of a composition containing, as the sole body slimming agent, at least one of α-tocopherol nicotinate, benzyl nicotinate, xanthinol nicotinate, hexyl nicotinate and α-tocopherol acetate, or a mixture thereof, said composition being free of any other lipolytic substance having caffeine-like activity.

More particularly, the present invention improves the esthetic appearance of a person through the slimming action of the above defined composition.

As is now well known, cellulitis is constituted by a local accumulation of fat and water trapped in a matrix having more or less tight compartments. This matrix is constituted of elements of a fundamental substance and more especially by proteoglycanes which are polymeric substances.

In order to liberate the trapped fats and water linked to this polymeric substance, it has been proposed to use, by local application, compositions based on enzymes which are capable of depolymerizing the proteoglycanes. These enzymes are mucopolysaccharidases and, more particularly, hyaluronidase, thiomucase and α-mucase.

Among the methods for stimulating lipolysis, the most commonly known and used is that which consists in inhibiting the phosphodiesterase in order to prevent or at least limit the rate of degradation of cyclic AMP. In effect, the phosphodiesterase destroys cyclic AMP by transforming it into 5' AMP so that it cannot function as a lipolysis activator.

It is important then to inhibit the activity of the phosphodiesterase in a manner so as to have a high amount of cyclic AMP on a level of the adipocytes thereby stimulating lipolytic activity.

Representative various phosphodiesterase inhibitors, which have been known as slimming agents, include in particular xanthic bases and more particularly theophylline, caffeine and theobromine.

Moreover, it has also been known to use certain oleosoluble vegetable extracts which, according to a different mechanism, can also act as a slimming agent. For instance, in U.S. Pat. No. 4,795,638 there is disclosed a thermo slimming cosmetic composition containing an oil-soluble plant extract having slimming action. Representative of these oil-soluble plant extracts are vegetable extracts including, principally, those of climbing ivy (*Hedera Helix*), arnica (*Arnica Montana*), rosemary (*Rosmarinus officinalis N*), marigold (*Calendula officinalis*), sage (*Salvia officinalis N*), ginseng (*Panax Ginseng*), St. Johns-wart (*Hypericum Perforatum*), ruscus (*Ruscus aculeatus*), meadowsweet (*Filipendula ulmaria L*) and orthosiphon (*Ortosifon Staminicus Benth*), as well as mixtures of these vegetable extracts.

In practice, these oleosoluble vegetable extracts having a slimming or lipolytic activity are most often associated with at least, one rubefacient substance which heats the skin upon application and promotes optimal diffusion of the oleosoluble vegetable extract toward their target, namely the unattractive bulges.

Representative rubefacient materials exhibiting such an activity include, principally, capsicum extracts, nicotinic acid salts such as triethanolamine nicotinate, nicotinic acid esters such as for example methyl, ethyl, hexyl, phenyl and benzyl nicotinate, as well as α-tocopherol nicotinate, nicotinyl alcohol and its organic acid esters such as, for example, nicotinyl tartarate or nicotinate.

These substances exhibiting a rubefacient activity of which certain ones cause a slight warming of the skin, deplete the water trapped in the cellulitic tissue and favor the removal of fatty acids from this tissue when there has been lipolysis and only after more heating, eventually caused by these substances, favors the diffusion of the active principles.

After extensive study it has now been noted, in a quite surprising manner, that certain ones of these rubefacient substances, in addition to their known activity on microcirculation, also exhibit excellent lipolytic activity.

This new property which had never been evidenced until now permits then to treat the undesirable effects of cellulitis and localized fatty excesses, without having recourse to the combined presence of an oleosoluble plant or vegetable extract having lipolytic activity or any other substance having lipolytic activity similar to caffeine.

The present invention thus relates to a new use of the nicotinate of α-tocopherol, benzyl, xanthinol or hexyl, or α-tocopherol acetate as a lipolytic substance having a caffeine-like activity for the preparation of a cosmetic or pharmaceutical composition having a slimming activity, the said composition being intended to combat cellulitis and localized fatty excesses and being free of any other substance having known caffeine-like activity and also being free of any oil-soluble plant extract having lipolytic activity.

In accordance with the present invention the lipolytic substance is generally present in an amount ranging from 0.1 to 10 percent by weight and preferably from 0.5 to 5 percent by weight based on the total weight of the composition.

The composition can be administered enterally, parenterally, rectally or topically.

When administered enterally, the medicine can be provided in the form of tablets, gelules, lozenges, syrups, suspensions, solutions, powders, granules or emulsions.

When administered parenterally, the compositions can be provided in the form of solutions or suspensions for perfusion or injection. When administered rectally the compositions can be provided in the form of suppositories.

When administered topically, these compositions can be provided under various forms and particularly in anhydrous form such as, for example, an oil or balm or even under the form of an oil-in-water or water-in-oil emulsion having the appearance of a cream or milk.

A preferred embodiment of the invention relates to a method for combatting cellulitis or reducing localized fatty excesses which comprises topically administering to a person having cellulitis or localized fatty excesses a body slimming amount of a composition containing, as the sole body slimming agent, at least one of α-tocopherol nicotinate, benzyl nicotinate, xanthinol nicotinate, hexyl nicotinate and α-tocopherol acetate, or a mixture thereof, said composition (a) being free of any other substance having lipolytic activity similar to caffeine, as well as being free of any oil-soluble plant extract having lipolytic or body-slimming activity and (b) being in the form of an oil, a balm, an oil-in-water emulsion or a water-in-oil emulsion and said body slimming agent being present in said composition in an amount ranging from 0.1 to 10 percent by weight based on the total weight of said composition.

When the composition is in anhydrous form the excipient can be a vegetable or animal oil, a mineral oil or even a synthetic oil, or mixtures of these oils.

Representative vegetable or animal oils, modified or not, include for example, sweet almond oil, avocado oil, ricin oil, olive oil, jojoba oil, perhydrosqualene, calophyllum oil, lanolin and its derivatives, turnsol oil, wheat germ oil, sesame oil, peanut oil, grape seed oil, soy oil, colza oil, safflower oil, cocoa oil, corn oil, shorea robusta fat, palm oil, and apricot stone oil.

Representative mineral oils include, for example, petrolatum oil and representative synthetic oils include ethyl and isopropyl palmitate, alkyl myristates such as isopropyl, butyl and cetyl myristate, hexyl stearate, triglycerides of octanoic and decanoic acids (for example the product sold under the trade name "Miglyol" by Dynamit Nobel), cetyl ricinoleate, stearyl octanoate (purcellin oil) and hydrogenated polyisobutene, as well as waxes such as ozokerite.

The fatty excipient can also contain certain compounds considered as fatty products, namely long chain alcohols such as cetyl alcohol, stearyl alcohol, myristyl alcohol, hydroxy stearyl alcohol, oleic alcohol or isostearyl alcohol.

When the compositions are provided in the form of an emulsion, the fatty phase of the emulsion represents from 10 to 80 percent by weight, the water phase from 15 to 80 percent by weight and the emulsifying agent from 5 to 30 percent by weight, based on the total weight of the emulsion.

The compositions according to the present invention can also contain various conventional adjuvants such as, for example, surface active agents, polymers, silicone oils, perfumes, dyes, sweetening agents, antioxidants or preservatives.

It is appropriate to note that hexyl nicotinate, due to its pronounced rubefacient properties, produces thermo-slimming compositions which are particularly agreeable on application to the skin.

Culture study of the lipolytic effect of active substances on adipose cells.

Adipose cells, contrary to adipocytes which are isolated from adipose tissue and which cease to be viable in a few hours, can be maintained up to three weeks without loss of viability (G. Ailhaud, Mol. Cell. Biochem., 49, 17–31, 1982).

The study has been carried out on differentiated Rat Ob cells cultivated under perfectly defined conditions (D. Gaillard et al, Biochem. Biophys. Acta, 846, 185–91, 1985 and A. Doglio et al, Biochem. J. 238, 123–129, 1986).

The lipolysis experiments have been conducted after exposure of the cells to labelled or $^{14}C$ acetate (2 stages of 48 hours in the presence of 0.5 µ Ci/culture dish). Under stationary state conditions, radioactivity is found principally in the fatty acids of triglycerides (R. Negrel et al, Proc. Natl. Acad. Sci., U.S.A., 75, 6054–6058, 1978 and C. Forest et al, Exp. Cell Res, 168, 218–232, 1987.

The lipolysis tests have been carried out at 37° C. in function of time. It is foreseen, at the minimum, 2 culture dishes per condition and 4 kinetic points, at the minimum, per culture dish.

The active substances have been tested alone and combined with caffeine. The concentrations are selected by viability tests (exclusion of TRYPAN Blue and spontaneous salting-out of cytoplasmic deshydrogenase lactate).

In the first stage the highest concentration of each molecule compatible with viability maintenance is used for the lipolysis tests.

In a second stage the molecules are studied in dose-response (7 concentrations per active substance, alone or combined, at different powers of 10 between $10^{-9}$ and $10^{-3}$ M).

In all cases the lipolysis activity of the active substances are compared to those obtained in the presence of a maximally stimulating concentration of two reference molecules: a β-adrenergic (isoprenaline) and caffeine at a concentration of $10^{-1}$ M (maximum non cytotoxic dose).

The results are set forth in the following table:

| X | Percentage of stimulation of the lipolysis of X alone | Percentage of stimulation of the lipolysis of X + caffeine |
| --- | --- | --- |
| α-tocopherol nicotinate | 100% | 46% |
| benzyl nicotinate | 100% | 45% |
| hexyl nicotinate | 35% | 35% |
| xanthinol nicotinate | 100% | 51% |
| α-tocopherol acetate | 50% | 35% |
| methyl nicotinate | ~0% | 35% |
| caffeine | 35% | — |

Note: 100% corresponds to the maximum effect of the isoprenaline (β-agonist) and to the maximum non cytotoxic effect of caffeine.

The values given in the table correspond to the maximum effect.

It can be seen from the above results, in a quite surprising manner, that α-tocopherol nicotinate, benzyl nicotinate, hexyl nicotinate, xanthinol nicotinate and α-tocopherol acetate exhibit excellent lipolytic activity which is higher than that of caffeine for most of these substances.

On the other hand, no lipolytic activity is observed with respect to methyl nicotinate. These studies show, moreover, that no notable synergy is observed and that in fact caffeine, when it is combined with these substances, inhibits lipolytic activity.

If hexyl nicotinate exhibits a lipolytic activity identical to that of caffeine, it possesses, nonetheless, the advantage of combining rubefacient properties so as to permit the production of thermo-slimming compositions.

There is now given as an illustration of the present invention and without any limiting character, several examples of compositions having a slimming activity containing, as the sole active slimming substance having a caffeine like activity, the nicotinates of α-tocopherol, benzyl and xanthinol and α-tocopherol acetate.

EXAMPLES OF COMPOSITIONS

Example 1—Slimming Balm

|  | wt percent |
| --- | --- |
| α-tocopherol nicotinate | 5 |
| Natural ozokerite | 20 |
| Liquid purcellin oil | 10 |
| White petrolatum | 15 |
| Preservative | 0.2 |
| Antioxidant | 0.3 |
| Petrolatum oil, sufficient amount for | 100 |

Example 2—Thermo-Slimming Body Oil

|  | wt percent |
| --- | --- |
| Hexyl nicotinate | 2 |
| Xanthinol nicotinate | 2 |

-continued

| | wt percent |
|---|---|
| "Miglyol 812" (Triglycerides of fatty acids, sold by Dynamit Nobel | 15 |
| Isopropyl palmitate | 10 |
| Sweet almond oil | 5 |
| Preservative | 0.2 |
| Perfume | 1 |
| Antioxidant | 0.1 |
| Petrolatum oil, sufficient amount for | 100 |

Example 3—Thermo-Slimming Foam

| | wt percent |
|---|---|
| Hexyl nicotinate | 1.5 |
| Cationic polymer sold under the trade name "Celquat L-200" by National Starch | 0.3 |
| Surface active agent, sold under the trade name "TWEEN 20" | 2 |
| Nonylphenol oxyethylenated with 12 moles of ethylene oxide | 10 |
| Ethyl acetate | 25 |
| Glycerine | 5 |
| Preservative | 0.3 |
| Water, sufficient amount for | 100 |

This composition (95 g) is packaged in an aerosol container in the presence of 5 g of butane as the propellant.

Example 4—Slimming Oil-In-Water Emulsion

| | wt percent |
|---|---|
| α-tocopherol | 2 |
| Silicone oil | 10 |
| Perhydrosqualene | 25 |
| 50/50 mixture of glycerol monostearate and polyethylene glycol 100 stearate, sold under the trade name "Arlacel 165" by Atlas | 6 |
| Polysorbate 60 | 2 |
| Cetyl alcohol | 1.2 |
| Stearic acid | 2.5 |
| Triethanolamine | 0.1 |
| Preservative | 0.3 |
| Antioxidant | 0.3 |
| Water, sufficient amount for | 100 |

Example 5—Slimming Clear Gel

| | wt percent |
|---|---|
| Benzyl nicotinate | 0.5 |
| Nonylphenol oxyethylenated with 12 moles of ethylene oxide | 5 |
| Crosslinked polyacrylic acid sold under the trade name "Carbopol 940" by Goodrich | 1 |
| Ethyl alcohol | 30 |
| Triethanolamine | 0.3 |
| Glycerine | 3 |
| Perfume | 0.3 |
| Preservative | 0.3 |
| Water, sufficient amount for | 100 |

The compositions of Examples 2 and 3, on application to the skin, cause a slight heating due to the rubefacient activity of hexyl nicotinate.

I claim:

1. A method of treating cellulitis or reducing localized fatty excesses on a body comprising topically applying on the part of the body to be treated which has cellulitis or localized fatty excesses, an effective body slimming amount of a composition containing, as the sole lipolytic or body slimming agent, a member selected from the group consisting of α-tocopherol nicotinate, benzyl nicotinate, xanthinol nicotinate, hexyl nicotinate, α-tocopherol acetate and a mixture thereof, said composition (a) being free of any other lipolytic substance having a phosphodiesterase inhibiting activity as well as being free of any oil-soluble plant extract having lipolytic or body slimming activity and (b) being in the form of an oil, a balm, an oil-in-water emulsion or a water-in-oil emulsion, and said body slimming agent being present in said composition in an amount ranging from 0.1 to 10 percent by weight based on the total weight of said composition so as to reduce localized fatty excess on said part of the body.

2. The method of claim 1 wherein said body slimming agent is present in said composition in an amount ranging from 0.5 to 5 percent by weight based on the total weight of said composition.

3. The method of claim 1 wherein said composition also includes at least one of a surface active agent, a polymer, a silicone oil, a perfume, a dye, an antioxidant or a preservative.

4. A method for treating cellulitis or reducing localized fatty excesses on a body comprising enterally administering to a person having cellulitis or localized fatty excesses a body slimming amount of a composition containing as the sole lipolytic or body slimming agent at least one of α-tocopherol nicotinate, benzyl nicotinate, xanthinol nicotinate, hexyl nicotinate and α-tocopherol acetate or a mixture thereof, said composition being free of any other lipolytic substance having a phosphodiesterase inhibiting activity and being in the form of a tablet, gelule, lozenge, syrup, suspension, solution, powder, granule or emulsion and said body slimming agent being present in said composition in an amount ranging from 0.1 to 10 percent by weight based on the total weight of said composition.

5. A method for treating cellulitis or reducing localized fatty excesses on a body comprising rectally administering to a person having cellulitis or localized fatty excesses a body slimming amount of a composition containing as the sole lipolytic or body slimming agent at least one of α-tocopherol nicotinate, benzyl nicotinate, xanthinol nicotinate, hexyl nicotinate and α-tocopherol acetate or a mixture thereof, said composition being free of any other lipolytic substance having a phosphodiesterase inhibiting activity and being in the form of a suppository and said body slimming agent being present in said composition in an amount ranging from 0.1 to 10 percent by weight based on the total weight of said composition.

6. A method of treating cellulitis or reducing localized fatty excesses on a body comprising topically applying on the part of the body to be treated which has cellulitis or localized fatty excesses, an effective body slimming amount of a composition containing, as the sole lipolytic or body slimming agent, a member selected from the group consisting of α-tocopherol nicotinate, benzyl nicotinate, xanthinol nicotinate, hexyl nicotinate, α-tocopherol acetate and a mixture thereof, said composition (a) being free of theophylline, caffeine and theobromine as well as being free of any oil-soluble plant extract having lipolytic or body slimming activity and (b) being in the form of an oil, a balm, an oil-in-water emulsion or a water-in-oil emulsion, and said body slimming agent being present in said composition in an amount ranging from 0.1 to 10 percent by weight based on the total weight of said composition so as to reduce localized fatty excess on said part of the body.

7. A method for treating cellulitis or reducing localized fatty excesses on a body comprising enterally administering to a person having cellulitis or localized fatty excesses a body slimming amount of a composition containing as the sole lipolytic or body slimming agent at least one of α-tocopherol nicotinate, benzyl nicotinate, xanthinol nicotinate, hexyl nicotinate and α-tocopherol acetate or a mixture thereof, said composition being free of theophylline, caffeine and theobromine and being in the form of a tablet, gelule, lozenge, syrup, suspension, solution, powder, granule or emulsion and said body slimming agent being present in said composition in an amount ranging from 0.1 to 10 percent by weight based on the total weight of said composition.

8. A method for treating cellulitis or reducing localized fatty excesses on a body comprising rectally administering to a person having cellulitis or localized fatty excesses a body slimming amount of a composition containing as the sole lipolytic or body slimming agent at least one of α-tocopherol nicotinate, benzyl nicotinate, xanthinol nicotinate, hexyl nicotinate and α-tocopherol acetate or a mixture thereof, said composition being free of theophylline, caffeine and theobromine and being in the form of a suppository and said body slimming agent being present in said composition in an amount ranging from 0.1 to 10 percent by weight based on the total weight of said composition.

* * * * *